United States Patent
Banerjee et al.

(10) Patent No.: US 9,446,145 B2
(45) Date of Patent: Sep. 20, 2016

(54) CURCUMIN-ANTIBODY CONJUGATES AS ANTI-CANCER AGENTS

(75) Inventors: Probal Banerjee, Staten Island, NY (US); Raja Krishnaswami, Staten Island, NY (US)

(73) Assignee: RESEARCH FOUNDATION OF THE CITY UNIVERSITY OF NEW YORK, New York, NY (US)

( * ) Notice: Subject to any disclaimer, the term of this patent is extended or adjusted under 35 U.S.C. 154(b) by 0 days.

(21) Appl. No.: 13/513,348

(22) PCT Filed: Dec. 1, 2010

(86) PCT No.: PCT/US2010/058588
§ 371 (c)(1),
(2), (4) Date: May 13, 2013

(87) PCT Pub. No.: WO2011/068894
PCT Pub. Date: Jun. 9, 2011

(65) Prior Publication Data
US 2013/0224229 A1 Aug. 29, 2013

Related U.S. Application Data (60) Provisional application No. 61/265,780, filed on Dec. 2, 2009.

(51) Int. Cl.
*A61K 47/48* (2006.01)

(52) U.S. Cl.
CPC ......... *A61K 47/48384* (2013.01); *A61K 47/48* (2013.01); *A61K 47/48561* (2013.01); *A61K 47/48623* (2013.01)

(58) Field of Classification Search
None
See application file for complete search history.

(56) References Cited

U.S. PATENT DOCUMENTS

2013/0296527 A1* 11/2013 Raja et al. ............... 530/300

FOREIGN PATENT DOCUMENTS

| WO | WO0202582 | 1/2002 |
|---|---|---|
| WO | WO2004031122 | 4/2004 |
| WO | WO2008051474 | 5/2008 |
| WO | WO2009064485 | 5/2009 |

OTHER PUBLICATIONS

Maheshwari et al; "Multiple biological activities of curcumin: a short review." Life Sci. (2006) 78 p. 2081-2087.*
Aoki, Hirosh et al; "Evidence that curcumin supresses the growth of malginant gliomas in vitro and in vivo through induction of autophagy: role of akt and extracellular signal regulated kinase signaling pathways." Mol. Pharmacol. (2007) 72(1) p. 29-39.*
Anand, Preetha et al; "Bioavailability of curcumin: problems and promises." Mol. Pharma. (2007) 4(6) p. 807-818.*
Xie, Hongsheng and Blattler, Walter A; "In vivo behavior of antibody drug conjugates for the targeted treatment of cancer." Expert. Opin. Biol. Ther. (2006) 6(3) p. 281-291.*
Guillemard, Veronique and Saragovi, H. Uri; "Taxane antibody conjugates afford potent cytotoxicity, enhanced solubility, and tumor target selectivity." Canc. Res. (2001) 61 p. 694-699.*
Strojnik, Tadej et al; "Experimental model and immunohistochemical analyses of u87 human glioblastoma cell xenografts in immunosuppressed rat brains." Anticanc. Res. (2006) 26 p. 2887-2900.*
Vyas, Hemant K. et al; "Selective killing of leukemia and lymphoma cells ectopically expressing hcgbeta by a conjugate of curcumin with an antibody against hcgbeta subunit." Oncology (2009) 76 p. 101-111.*
Li, Zongwen et al; Human chorionic gonadotropin beta induces cellmotility via erk1/2 and mmp-2 activation in human glioblastoma u87mg cells. J. Neurooncol. (2013) 111 p. 237-244.*
Borlongan, Cesar V. et al; "Central nervous sytem entry of peripherally injected umbilical cord blood cells is not required for neuroprotection in stroke." Stroke (2004) 35 p. 2385-2389.*

(Continued)

*Primary Examiner* — Maury Audet
*Assistant Examiner* — Fred Reynolds
(74) *Attorney, Agent, or Firm* — Hoffmann & Baron, LLP (57) ABSTRACT

The invention relates to curcumin derivatives having the formula I: wherein: Z represents: $H_3CO$ A represents $—CH_2—CH_2—$ or $—CH=CH—$; L represents $—C(O)—(NH)_{n1}—R—(NH)_{n2}—C(O)—$; R represents a saturated or unsaturated, branched or unbranched hydrocarbyl chain having a minimum of 3 carbon atoms in the chain; wherein the maximum number of carbon atoms in the chain is 24; and wherein the carbon atoms of the chain can be replaced by at least one heteroatom, wherein the heteroatoms are independently $—O—$ or $—NH_2—$, with the proviso that each heteroatom is separated from each other heteroatom by at least two carbon atoms; n1 and n2 independently represent 0 or 1; and Y represents an antibody that binds specifically to a target antigen of a tumor cell. The invention further relates to methods of method of inhibiting the growth of tumors in a human by administering an effective amount of the curcumin derivative, and to methods of producing the curcumin derivative.

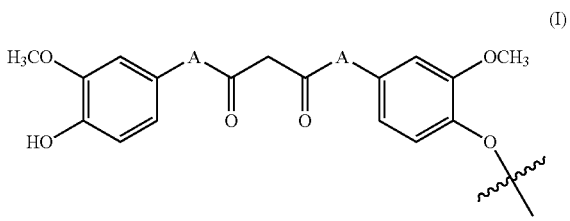

(I)

17 Claims, 5 Drawing Sheets

(56) References Cited

OTHER PUBLICATIONS

Rascher, Gesa et al; "Extracellular matrix and the blood brain barrier in glioblastoma multiforme: spatial segregation of tenascin and agrin." Acta Neuropathol. (2002) 104 p. 85-91.*

Tedesco, S. et al, "Protocols of human macrophage differentiation and activation: pharmacological modulation by curcumin analogues." 37th Congress, National Italian Pharmacology Society, (2015), abstract 588, available online at http://congresso.sifweb.org/abs/588.pdf.*

Database ZCAPLUS [online] Chemical Abstract Service, XP002639554.

Shiv Kumar Dubey et al., Novel Method for Preaparation of Monoesters of Symmetric Diphenolic Compounds Like Curcumin (1,7-Bis(4-hydroxy-3-methoxy phenyl)-1,6-heptadiene-3,5-dione) via Solid-Phase Synthesis, vol. 37, No. 23 (2007), XP009148714.

Shiv K. Dubey et al., "Design, Synthesis and Characterization of Some Bioactive Conjugates of Curcumin with Glycine, Glutamic Acid, Valine and Demethylenated Piperic Acid and Study of Their Antimicrobial and Antiproliferative Properties", vol. 43, No. 9 (2007), XP002639535.

* cited by examiner

CURCUMIN-ANTIBODY CONJUGATES AS ANTI-CANCER AGENTS

CROSS-REFERENCE TO RELATED APPLICATION

This application is the U.S. National Phase of, and claims priority to, International Patent Application Number PCT/US2010/058588 filed 1 Dec. 2010, which claims the benefit of U.S. Provisional Application No. 61/265,780, filed Dec. 2, 2009, which is incorporated herein by reference.

BACKGROUND OF THE INVENTION

Cancer is one of the scourges of human existence. Although chemotherapeutic agents that are effective in treating malignant tumors are known, such agents generally cause severe side effects.

For example, brain cancer is generally associated with a particularly grim prognosis. The average survival rate from brain cancer is barely two years, and the entire therapeutic procedure of tumor resection followed by chemo- and/or radiation therapy is extremely painful and causes many side effects.

Curcumin is a component of the culinary ingredient turmeric, and has the chemical name 1,7-bis(4-hydroxy-3-methoxyphenyl)-1,6-heptadiene-3,5-dione. Curcumin directly inhibits a group of active proteins and also indirectly modulates other crucial enzymes and transcription factors that promote tumor cell survival and proliferation. Being able to selectively inhibit a large number of cell cycle- and tumor-promoting proteins, it is likely that curcumin attacks cancer cells by simultaneously regulating multiple pathways. Spectroscopic analyses have shown that curcumin is taken up more rapidly by tumor cells and the amount of curcumin taken up by the cancer cells is directly proportional to cell death. (Kunwar, A., Batik, A., Mishra, B., Rathinasamy, K., Pandey, R., and Priyadarsini, K. I. *Biochimica et Biophysica Acta (BBA)—General Subjects* 1780, 673-679) (2008). Accordingly, curcumin is toxic to cancer cells, but is generally non-toxic to non-transformed cells. Purkayastha, S., Berliner, A., Fernando, S. S., Ranasinghe, B., Ray, I., Tariq, H., and Banerjee, P., *Brain Research* 1266C, 130-138 (2009); and Dhandapani, K. M., Mahesh, V. B., and Brann, D. W. *J. Neurochem.* 102, 522-538 (2007).

Although curcumin is harmless to most normal cells, its administration to humans is somewhat restricted by its poor solubility in water and also by its rapid metabolism in the body (Purkayastha, S., Berliner, A., Fernando, S. S., Ranasinghe, B., Ray, I., Tariq, H., and Banerjee, P., *Brain Research* 1266C, 130-138) (2009)). Various solubilized versions of curcumin (involving biocompatible solvents or incorporation into appropriate nanoparticles) have been prepared and such formulations are being tested currently. See Carter, *Journal of the National Cancer Institute* 100, 616-617 (2008); Singh, *Cell* 130, 765-768 (2007); and Purkayastha, S., Berliner, A., Fernando, S. S., Ranasinghe, B., Ray, I., Tariq, H., and Banerjee, P., *Brain Research* 1266C, 130-138 (2009).

Nevertheless, the administration of solubilized curcumin still leaves open the possibility of losing significant amounts of the injected curcumin through metabolic breakdown even before it reaches the target cancer cells. Consequently, reaching a high concentration of curcumin in the cancer cells remains difficult through such strategies.

State-of-the-art targeting antibodies are also known. Such antibodies are capable of directing chemotherapeutic drugs to tumor cells. If made in mammals other than humans, targeting antibodies can be humanized. Alternatively, human antibodies developed using transgenic mice and phage display are also known (McCafferty et al., *Nature* 348, 552-554 (1990); Lonberg, N. *Nat Biotech* 23, 1117-1125 (2005); Reichert et al., *Nature Biotechnology* 23, 1073-1078 (2005); Senter, P. D. *Current Opinion in Chemical Biology* 13, 235-244 (2009); and Reichert et al., *Nature Reviews. Drug Discovery* 6, 349-356 (2007)).

However, cancer researchers generally use antibody-mediated targeting only if the anticancer agent is toxic toward normal cells. For example, the increasing use of targeted anticancer agents that inhibit tyrosine kinase signaling (monoclonal antibodies or tyrosine kinase inhibitors) (trastuzumab, sunitinib) has dramatically improved the survival of patients with malignancies, but cardiotoxicity, including heart failure, left ventricular dysfunction, hypertension, myocardial infarction, and thromboembolism, has accompanied such treatment (Chen, *Current Cardiology Reports* 11, 167-174 (2009).)

Similarly, other anticancer agents currently used or being developed for antibody targeting such as maytansinoids, calicheamycin, or auristatins (Fennell et al., *J. Antimicrob. Chemother.* 51, 833-841 (2003)); Tassone et al., *Blood* 104, 3688-3696 (2004); and Tassone et al., *Cancer Res* 64, 4629-4636 (2004) belong to this category in which the untargeted form of each drug is toxic toward normal cells (Ikeda et al., *Clinical Cancer Research* 15, 4028-4037 (2009); van der Velden, et al., *Blood* 97, 3197-3204 (2001); and Law et al., *Clinical Cancer Research* 10, 7842-7851 (2004)). Consequently, it is difficult to eliminate the side effects of these targeted agents at higher doses, which are often required in aggressive treatment of cancer.

SUMMARY OF THE INVENTION

In a first aspect, the invention relates to a curcumin derivative having the formula I:

$$Z\text{-}L\text{-}Y \qquad (I)$$

wherein:
Z represents:

L represents —C(O)—(NH)$_{n1}$—R—(NH)$_{n2}$—C(O)—;

R represents a saturated or unsaturated, branched or unbranched hydrocarbyl chain having a minimum of 3 carbon atoms in the chain; wherein the maximum number of carbon atoms in the chain is 24; and wherein the carbon atoms of the chain can be replaced by at least one heteroatom, wherein the heteroatoms are independently —O— or —NH$_2$—, with the proviso that each heteroatom is separated from each other heteroatom by at least two carbon atoms; n1 and n2 independently represent 0 or 1; and
Y represents an antibody that binds specifically to a target antigen of a tumor cell.

In a second aspect, the invention relates to a method of inhibiting the growth of tumors in a human in need thereof, the method comprising administering to the human an effective amount of a curcumin derivative having the formula I according to the first aspect above.

In a third aspect, the invention relates to a method of producing a curcumin derivative having the formula I according to the first aspect above. The method comprises:
(a) treating the curcumin derivative with a cyclic carboxylic acid anhydride under conditions that produce Z-L-OH wherein n1 and n2 represent 0;
(b) treating the Z-L-OH from step (a) with N-hydroxysuccinimide under conditions that produce the corresponding succinimidyl ester;
(c) treating the succinimidyl ester of step (b) with an antibody that binds specifically to a target antigen of a tumor cell under conditions that produce Z-L-Y wherein n1 and n2 represent 0.

Structure Z in formula I represents curcumin when A represents —CH═CH— and tetrahydrocurcumin when A represents —CH$_2$—CH$_2$—.

DESCRIPTION OF THE FIGURES

FIG. 5: Curcumin-CD68 adduct causes shrinkage of GL261 brain tumors:
Round 1 (4 per group): 37.5 pmole Ab-linked curcumin injected on days 15 and 17 after implantation of 5×10$^5$ GL261 cells. A significant reduction in tumor size was not observed.
Round 2 (3 per group): 750 pmole Ab-linked curcumin injected on days 8, 11, and 14 after implantation of 5×10$^5$ GL261 cells. A significant reduction in tumor size was observed.
Round 3 (3 per group): Same as Round 2, but the injection of Ab-linked curcumin was performed on days 13 and 15. A significant reduction in tumor size was observed.

DETAILED DESCRIPTION OF THE INVENTION

Linker

The linker L covalently joins the curcumin residue Z to the antibody Y, and has the formula —C(O)—(NH)$_{n1}$—R—(NH)$_{n2}$—C(O)—. In the linker formula, n1 and n2 independently represent 0 or 1.

R in the linker formula represents a branched or unbranched hydrocarbyl chain (i.e. alkyl, alkenyl, or alkynyl) having a minimum of 3 carbon atoms in the chain. The maximum number of carbon atoms in the chain is 24, preferably 12, and more preferably 8. The carbon atoms of a chain can all be saturated, or can all be unsaturated. Alternatively, the chain can comprise a mixture of saturated and unsaturated carbon atoms. The unsaturated hydrocarbyl chains contain one or more double and/or triple bonds. In addition, the carbon atoms in the hydrocarbyl chain may optionally be replaced by at least one heteroatom, wherein the heteroatoms are independently —O— or —NH$_2$—; and wherein each heteroatom is separated from each other heteroatom by at least two carbon atoms.

Some examples of suitable saturated straight hydrocarbyl chains include n-propylene (—CH$_2$CH$_2$CH$_2$—), n-butylene, n-pentylene, n-hexylene, n-decylene, n-hexadecylene, and n-octadecylene chains. Some examples of suitable unsaturated straight hydrocarbyl chains include 2-butenylene (—CH$_2$CH═CHCH$_2$—), 1,3-heptadienylene, 2-dodecenylene, oleylene, linoleylene, and linolenylene chains.

Some examples of suitable saturated, branched hydrocarbyl chains include iso-butylene (—CH$_2$CH(CH$_3$)CH$_2$—), sec-butylene, 3-methyl-1-butylene, neopentylene, 3-methyl-2-pentylene, and 2-methyl-5-ethyl-1-decylene. Some suitable examples of unsaturated, branched alkyl groups include 4-methyl-2-pentenylene (—CH$_2$CH(CH$_3$)CH═CHCH$_2$—) and 7-ethyl-1,3-hexadecadienylene.

Some examples of suitable groups wherein the carbon atoms in the hydrocarbyl chain are replaced by at least one heteroatom include 3-oxa-1,5-pentylene (—CH$_2$CH$_2$OCH$_2$CH$_2$—), 3,6-dioxa-1,8-octylene and 2,4-diaza-1,6-hexylene.

The saturated or unsaturated, branched or unbranched hydrocarbyl chain of R may include, in whole or in part, a ring having 6-10 members, and preferably having six members. Some examples of suitable groups wherein the saturated or unsaturated, branched or unbranched hydrocarbyl chain of R includes a ring include 1,4-phenylene, 1,2-phenylene, 1,1'-biphenyl, 1,4-cyclohexylene, 1,4-cyclohexadienylene, 1,4-cyclohexenylene, —CH$_2$-Ph-CH$_2$—, and —CH$_2$—CH$_2$-Ph- (wherein Ph represents a 1-4-phenylene group).

The linker may, for example, be derived from a molecule that has at least two functional groups, at least one of which is able to form a covalent bond with a hydroxyl group on the curcumin moiety, and at least one of which is able to form a covalent bond with a free amino group on a lysine residue of an antibody. The functional groups may be the same or different.

In one embodiment, the linker is derived from, or has a structure that can be derived from, a molecule that has the formula:

wherein X$^1$ is a functional group that forms a covalent bond with a hydroxyl group on the curcumin moiety, and X$^2$ is a functional group that forms a covalent bond with the free amino group on a lysine residue of an antibody, and R is any R group in the linker formula described above. The X$^1$ and X$^2$ functional groups may be the same or different.

Suitable examples of X$^1$ and X$^2$ functional groups include isocyanate groups and functional groups having the formula —C(O)X$^3$, wherein X$^3$ represents a halide group, e.g., chloride or bromide; an alkoxy ester group, e.g., methoxy or ethoxy; a sulfonate ester group, e.g., p-toluenesulfonate, benzenesulfonate, or methanesulfonate; or a succinimidyloxy group.

Alternatively, X$^1$ and X$^2$ join to form a cyclic carboxylic acid anhydride. Suitable cyclic carboxylic acid anhydrides include succinic anhydride, glutaric anhydride, maleic anhydride, adipic anhydride, and phthalic anhydride.

Some suitable diisocyanates include 1,3-propylene diisocyanate, 1,6-hexamethylene diisocyanate, 1,8-octamethylene diisocyanate; 3,6-dioxaoctane-1,8-diisocyanate and 2,4-diazahexane-1,6-diisocyanate. Some additional examples of functional groups include the acid chlorides and activated esters of glutaric, adipic, and phthalic acids. Activated esters include the p-toluenesulfonate, benzenesulfonate, methanesulfonate, and N-hydroxysuccinimide (NHS) esters of glutaric, adipic, and phthalic acids.

A preferred method of linking the curcumin moiety Z to the antibody Y is to react curcumin with a cyclic carboxylic acid anhydride, such as glutaric anhydride or adipic anhydride, and then to convert the resulting curcumin monocarboxylic acid to an activated ester, preferably the succinimidyl ester, followed by replacing the succinimidyloxy group with the amino group of a lysine residue of antibody Y.

Thus, depending upon the function groups on the protein and on the linking agent, one can form a —(NH)$_n$—C(O)— group between the linker and the curcumin moiety or the antibody, wherein n is 0 when the functional group has the formula —C(O)X$^3$ and n is 1 when the functional group is isocyanate. Accordingly, a phenolic hydroxy group from the curcumin moiety and an amino group from antibody Y bond to an acyl group of L when n1 and n2 are 0, and to a carbamoyl group of L when n1 and n2 are 1.

Antibody

In this specification, an antibody is defined broadly as a protein that binds specifically to an epitope of an antigen. Such antibodies contain regions that bind specifically to an epitope, called an antibody hypervariable region. The antibody may further comprise an entire antibody variable region. The antibody may still further comprise an antibody constant region. Antibodies include, for example, a whole antibody, an antibody fragment, a chimerized antibody or a humanized antibody.

The antibody is preferably a monoclonal antibody. The antibody may be further genetically or chemically modified. For use in humans, the antibody is preferably chimerized or humanized.

Suitable variable and hypervariable regions of non-human antibodies may be derived from antibodies produced by any non-human mammal from which monoclonal antibodies can be derived. Suitable examples of mammals other than humans include rabbits, rats, mice, horses, goats, or primates. Preferably, the antibodies are human antibodies produced in a transgenic mammal, preferably a mouse. An example of such a transgenic mouse is the so-called XenoMouse™ (Abgenix/Amgen, Freemont, Calif.) described by Green, L L., "Antibody Engineering Via Genetic Engineering of the Mouse: XenoMouse Stains are a Vehicle for the Facile Generation of Therapeutic Human Monoclonal Antibodies," J. Immunol. Methods," 10; 231(1-2):11-23 (1999). See also Aya Jakobovits, "From XenoMouse technology to panitumumab, the first fully human antibody product from transgenic mice," Nature Biotechnology 25, 1134-1143 (2007).

Antibody fragments have binding characteristics that are the same as, or are comparable to, those of the whole antibody. Suitable fragments of the antibody include any fragment that comprises all or a sufficient portion of the hypervariable (i.e. complementary determining) region to bind specifically, and with sufficient affinity, to a desired epitope.

The preferred fragments are single chain antibodies (scFv), which are polypeptides that comprise at least the variable region of the heavy chain of the antibody and the variable region of the light chain, with or without an interconnecting linker. Single chain antibodies are made by methods well known in the art. See, for example, M. D. Sheets, "Efficient construction of a large nonimmune phage antibody library: The production of high-affinity human single-chain antibodies to protein antigens," Proc. Natl. Acad. Sci. 95, 6857-6162 (1998).

A chimerized antibody comprises the variable region of a non-human antibody and the constant region of a human antibody. A humanized antibody comprises the hypervariable region (CDRs) of a non-human antibody. The variable region other than the hypervariable region, e.g. the framework variable region, and the constant region of a humanized antibody are those of a human antibody.

The antibodies and functional equivalents may be members of any class of immunoglobins, such as: IgG, IgM, IgA, IgD or IgE, and the subclass thereof. The functional equivalents may also be equivalents of combinations of any of the above classes and subclasses.

The hypervariable regions of the antibodies bind specifically with a target antigen of a tumor cell. The tumor cell is any tumor cell that is sensitive to curcumin. The tumor may, for example, be a tumor of any organ or other part of a human body, e.g., colon, lung, head and neck, breast, cervix, prostate, tongue, skin (especially melanoma), blood (especially multiple myeloma), etc.

In a preferred embodiment, the antibody binds to a target antigen of a brain tumor. The brain tumor may be primary, e.g., glioma or neuroblastoma, or metastatic from any organ mentioned above, e.g., melanoma. Some examples of target antigens of glioblastomas include CD68, MHC Class I (MHC-I), CD133, Plasmalemmal vesicle associated protein-1 (PV-1), CD90, CD44, CX3CR1, GLUTS, and EphA2. Some examples of target antigens of melanoma cells include MUC18, and ABCB5. Some examples of target antigens of neuroblastomas include NB-p260, or 4Ig-B7-H3.

These, and other, antigens are known to those of skill in the art. For example:

Glioblastoma Antigens:

CD68: Strojnik et. al. (2009) Anticancer Research, 29, 3269-3280.

MHC-I: Elizabeth W. Newcomb, Sandra Demaria, Yevgeniy Lukyanov, Yongzhao Shao, Tona Schnee, 1Noriko Kawashima, Li Lan, J. Keith Dewyngaert, David Zagzag, William H. McBride, and Silvia C. Formenti (2006) Clin Cancer Res, 12, 4730-4737.

CD133: Roger Stupp & Monika E Hegi (2007) Nature Biotechnology, 25, 193-194.

Plasmalemmal vesicle associated protein-1 (PV-1): Eleanor B. Carson-Walter, Jessica Hampton, Eveline Shue, Daniel M. Geynisman, Pramod Kumar Pillai, Ramasri Sathanoori, Stephen L. Madden, Ronald L. Hamilton, and Kevin A. Walter (2005) Clin Cancer Res., 11, 7643-7650.

CD90: Tumorigenesis of Chemotherapeutic Drug-Resistant Cancer Stem-Like Cells in Brain Glioma. *Stem Cells and Development,* 16, 837-847.

CD90 and CD44: Primary Glioblastomas Express Mesenchymal Stem-Like Properties. Molecular Cancer Research, 4, 607-619 (2006).

CX3CR1: Che Liu, Defang Luo, Wolfgang J. Streit, Jeffrey K. Harrison Journal of Neuroimmunology 198 (2008) 98-105.

GLUTS: Neuropathology and Applied Neurobiology (2004), 30, 447-455.

EphA2: Jill Wykosky, Denise M. Gibo, Constance Stanton, and Waldemar Debinski Mol Cancer Res (2005) 3, 541-551.

Melanoma Antigens:

Muc18: Gwladys Zabouo1, Anne-Marie Imbert1,2, Jocelyne Jacquemier, Pascal Finetti, Thomas Moreau1, Benjamin Esterni, Daniel Birnbaum4, François Bertucci and Christian Chabannon Breast Cancer Research Vol 11, 1-14.

Jurgen M. Lehmann, Gert Riethmuller, and Judith P. Johnson (1989) Proc. Natl. Acad. Sci. USA Vol. 86, pp. 9891-9895.

ABCB5: Tobias Schatton, George F. Murphy, Natasha Y. Frank, Kazuhiro Yamaura, Ana Maria Waaga-Gasser, Martin Gasser, Qian Zhan, Stefan Jordan, Lyn M. Duncan, Carsten Weishaupt, Robert C. Fuhibrigge, Thomas S. Kupper, Mohamed H. Sayegh & Markus H. Frank (2008) Nature, 451, 345-351.

Neuroblastorna Antigens:

NB-p260: K. David, 1 A. Ehrhardt, 1, R. Erttmann, R. Bredehorst and C.-W. Vogel (1997) Eur J Cancer, Vol. 33, No. 12, pp. 1937-1941.

4Ig-B7-H3: Roberta Castriconi, Alessandra Dondero, Raffaella Augugliaro, Claudia Cantoni, Barbara Carnemolla, Angela Rita Sementa, Francesca Negri, Romana Conte, Maria Valeria Corrias, Lorenzo Moretta, Alessandro Moretta, and Cristina Bottino PNAS (2004) 101, 12640-12645.

Administration

The curcumin-antibody conjugates of the invention are administered by methods known in the art (In this specification, the words "conjugate(s)" and "adduct(s)" are used interchangeably). For example, the conjugate may be administered enterally or parenterally. Enteral administration includes, for example, oral and rectal administration. Parenteral administration includes, for example, intra-venous, intra-arterial, intra-muscular, and subcutaneous administration.

A preferred method of administration, especially for brain tumors, is direct intracranial infusion from an osmotic pump connected to a cannula or catheter. A suitable technique is convection-enhanced drug delivery, in which drugs are administered by slow infusion of a drug into the target area of the brain (e.g., into a tumor) at a rate that allows the intracranial pressure to be maintained within normal limits and enables uniform, local distribution of the infusate against interstitial pressure. Drugs are delivered continuously by means of an intracranial cannula or catheter. See, for example, "Convection-enhanced delivery of macromolecules in the brain, PNAS 91(6), 2076-2080 (1994), "Salirasib (farnesyl thiosalicylic acid) for brain tumor treatment: a convection-enhanced drug delivery study in rats," Molecular Cancer Therapeutics 7(11,) 3609-3616 2008), "Convection-Enhanced Delivery for the Treatment of Pediatric Neurologic Disorders," J Child Neurol 23(10,) 1231-1237 (2008), "Intracerebral infusion of an EGFR-targeted toxin in recurrent malignant brain tumors," Neuro Oncol 10(3), 320-329 (2008), Convection-enhanced delivery of maghemite nanoparticles: Increased efficacy and MRI monitoring. Neuro Oncol 10(2), 153-161 (2008), "Direct Intracerebral Delivery of Cintredekin Besudotox (IL13-PE38QQR) in Recurrent Malignant Glioma: A Report by the Cintredekin Besudotox Intraparenchymal Study Group. JCO 25(7), 837-844 (2007).

In an embodiment of the invention, substantially all tumor cells in a patient are eliminated by the administration of a curcumin-antibody conjugate described above. Following substantial elimination of all tumor cells, a solubilized form of curcumin in an amount effective to slow the growth of any remaining tumor cells is administered. In this specification, the phrase "substantially all tumor cells" means at least about 95%, and preferably at least about 99% of tumor cells. A solubilized form of curcumin refers to curcumin dissolved in a non-toxic solvent in which an effective amount of curcumin is soluble, or a solubilized curcumin derivative described (but not necessarily claimed) in PCT application US2007/021805 or in published U.S. patent application 2010/0240905. The solubilized curcumin derivatives described (but not necessarily claimed) in PCT application US2007/021805 and in published U.S. patent application 2010/0240905 are incorporated herein by reference. A non-toxic solvent in which an effective amount of curcumin is soluble is a solvent that, following administration, results in 0.05-0.125% DMSO in body fluid, e.g., blood, which is able to retain up to 50 μM concentration of curcumin in solution. For example, the administration of 5 μl of 3 mM curcumin in a solution of 3% DMSO in phosphate-buffered saline (PBS) is diluted to this concentration of DMSO and 35 μM curcumin in the brain.

A non-toxic solvent in which an effective amount of curcumin is soluble includes, for example, 3% DMSO in phosphate-buffered saline (PBS).

In another embodiment, the administration of a curcumin-antibody conjugate described above is accompanied by the further administration of at least one additional anti-cancer chemotherapeutic agent. Preferably, the additional anti-cancer chemotherapeutic agent is approved by an agency authorized to approve drugs, such as the United States Food and Drug Administration.

Some examples of additional anti-cancer chemotherapeutic agents include carboplatin, cisplatin, cyclophosphamide, docetaxel, doxorubicin, erbitux, erlotinib, etoposide, fluorouracil, gemcitabine, herceptin, imatinib, irinotecan mesylate, irinotecan, methotrexate, paclitaxel, sorafinib, sunitinib, topotecan, vinblastine, and vincristine. Some examples of additional anti-cancer chemotherapeutic agents for brain cancer include Temodar, Avastin, Matulane, Gliadel, and BiCNU.

The additional anti-cancer chemotherapeutic agent or agents may be administered before or after (e.g., 1-4 days, 1-4 weeks, or 1-4 months before or after) administration of the curcumin-antibody conjugate. Alternatively, administration of the additional anti-cancer chemotherapeutic agent or agents overlaps administration of the curcumin-antibody conjugate.

The additional anti-cancer chemotherapeutic agents mentioned above display a significant level of toxicity and, consequently, a spectrum of serious side effects. Administration of the curcumin-antibody adduct of the invention before, during, or after treatment with such chemotherapeutic drugs is expected to require a diminished dose of the toxic chemotherapeutic agent, and thus decreasing its side effects.

Miscellaneous

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any two, three, or four of the members, e.g., a and c; a, d, and e; b, c, d, and e; etc.

In some cases, the members of a first group of parameters, e.g., a, b, c, d, and e, may be combined with the members of a second group of parameters, e.g., A, B, C, D, and E. In such cases, any member of the first group or of a sub-group thereof may be combined with any member of the second group or of a sub-group thereof to form additional groups, i.e., b with C; a and c with B, D, and E, etc.

For example, in the present invention, groups of various parameters are defined (e.g., Z, A, L, R, n1, n2, Y, etc.). Each group contains multiple members. For example, some examples of suitable saturated straight hydrocarbyl chains within the definition of R are said to include seven members, i.e., n-propylene, n-butylene, n-pentylene, n-hexylene, n-decylene, n-hexadecylene, and n-octadecylene chains. Any one member, or any and all possible sub-groups of 2-6 members are specifically contemplated, e.g., n-propylene and n-hexylene; n-butylene, n-decylene, and n-octadecylene; n-propylene, n-hexylene, n-decylene, and n-hexadecylene; and n-propylene, n-pentylene, n-hexylene, n-decylene, n-hexadecylene, and n-octadecylene chains.

The instant invention further contemplates embodiments in which each element or sub-group of elements listed under one group may be combined with each and every element listed or sub-group of elements under any other group. For example, A is said to represents —CH$_2$—CH$_2$— or —CH═CH—; while n1 is said to represent 0 or 1. Accordingly, embodiments include those wherein A represents —CH$_2$—CH$_2$— and n1 represents 0; A represents —CH$_2$—CH$_2$— and n1 represents 1; A represents —CH═CH— and n1 represents 0; and A represents —CH═CH— and n1 represents 1.

With each group, it is specifically contemplated that any one or more members can be excluded. For example, some examples of suitable groups wherein carbon atoms in a hydrocarbyl chain are replaced by at least one heteroatom are said to include 3-oxa-1-5-pentylene, 3,6-dioxa-1-8-octylene and 2,4-diaza-1,6-hexylene. Accordingly, Sub-groups include 3-oxa-1-5-pentylene and 3,6-dioxa-1-8-octylene; 3-oxa-1-5-pentylene and 2,4-diaza-1,6-hexylene; and 3,6-dioxa-1-8-octylene and 2,4-diaza-1,6-hexylene.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

A list following the word "comprising" is inclusive or open-ended, i.e., the list may or may not include additional unrecited elements. A list following the words "consisting of" is exclusive or closed ended, i.e., the list excludes any element not specified in the list.

EXAMPLES

Example 1

Synthetic Modification of Curcumin for Targeting

1A) Conversion of Curcumin to Curcumin Monocarboxylic Acid curcumin monocarboxylic acid To a solution of 4 g (10.86 mmol) of curcumin, and 330 mg (2.71 mmol) of 4-dimethylaminopyridine (DMAP) in 140 ml tetrahydrofuran (THF), 2.27 ml (16.29 mmol) of Et$_3$N was added. 1.42 g (12.49 mmol) of glutaric anhydride (95%) in 10 mL THF was slowly added dropwise to the curcumin solution. The mixture was stirred and refluxed under N$_2$ atmosphere for 48 hrs. THF was removed under vacuum, redissolved in 100 mL CHCl$_3$ and washed with 100 mL 0.1 N HCl followed by water (3×50 mL) and brine (3×50 mL). The organic layer was separated and dried over anhydrous Na$_2$SO$_4$. The product was purified via column chromatography, eluting with CHCl$_3$:EtOAc (95:5) and isolated as orange powder. Yield: 64%. $^1$H NMR (CDCl$_3$), δ (ppm): 2.10-2.12 (t, 2H); 2.56-2.58 (t, 2H); 2.69-2.72 (t, 2H); 3.87 (s, 3H); 3.94 (s, 3H); 5.83 (s, 2H); 6.48-6.57 (t, 2H); 6.48-6.57 (m, 1H); 6.94-7.16 (m, 5H); 7.59-7.62 (d, 2H). MS (ESI) calcd. for C$_{26}$H$_{26}$O$_9$: 482.48. found: 483.2 [M+H]$^+$.

1B) Convrsion of Curcumin Carboxylic Acid to Succinimidyl Curcumin Carboxylate curcumin monocarboxylic acid curcumin monocarboxylic acid NHS ester

To a solution of 500 mg (1.04 mmol) of curcumin COOH in 15 ml dimethylformamide (DMF), 120 mg (1.04 mmol) of N-Hydroxysuccinimide (NHS) was added. While stirring, 309 mg (1.5 mmol) of dicyclohexylcarbodiimide (DCC) in 2 ml DMF was added dropwise at 0° C. The mixture was stirred at room temperature under $N_2$ atmosphere for 12 hours. The dicyclohexylurea formed was filtered out, the solvent was evaporated to a small volume, and the residue was completely precipitated by adding excess diethyl ether. The ether was evaporated, and the product was purified via column chromatography, eluting with $CHCl_3:CH_3OH$ (98:2). Yield: 47% $^1H$ NMR information in step A, new group-1.71-2.12 (t, 4H).

Example 2

Curcumin-Antibody Complex

2A) Coupling Curcumin Carboxylate with Muc18 Antibody succinimidyl curcumin carboxylate lysine (antibody)

curcumin-MUC18 molecule
R = curcumin carboxylate

Succinimidyl curcumin carboxylate (0.3 mg) was dissolved in 2 ml of DMSO, and 5 µl of this solution was diluted to 8 µl in dimethylsulfoxide (DMSO). The solution was added dropwise to 100 µl of the MUC18 antibody (straight from stock) while vortexing to prevent precipitation. Mixture was stirred for four hours. A standard DyLight protein labeling kit and procedure was used to attach the appropriate dye to the MUC18-curcumin molecules for cell imaging purposes (800 nm for in vivo work, 633 nm for in vitro work).

2B) Quantification of Curcumin: MUC18 Molar Ratio Using UV Spectroscopy

UV absorbance and molar extinction coefficients were used to quantify the curcumin: MUC18 molar ratio. The absorbance of the product in phosphate buffered saline solution was measured at 280 nm for MUC18, and 430 nm for curcumin. If the values obtained were not in the linear range (0.2-1), the solution was further diluted. The absorbance measured for each molecule was divided by the appropriate molar extinction coefficient (MUC18: $2.1 \times 10^5$ $M^{-1}$ $cm^{-1}$, curcumin: $4.88 \times 10^4$ $M^{-1}$ $cm^{-1}$), giving the molar concentrations of each molecule. The molar ratio was determined by setting the molar concentrations as a ratio and simplifying to smallest whole numbers.

Example 3

Reduction of B16F10 Melanoma Cells with Curcumin-MelCAM (MUC18) Antibody-Dylight800 Adduct In Vitro and In Vivo 3A) Curcumin-MUC18 IC50—Determining Concentration Required for 50% B16F10 Melanoma Cell Death.

Figure 1:
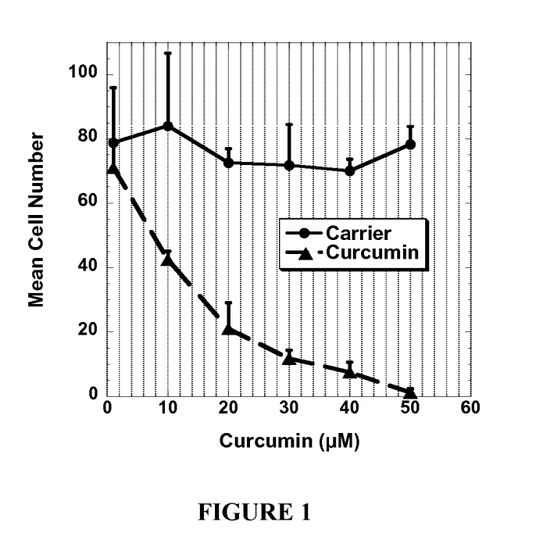
FIG. 1: The IC50 for the effect of solubilized curcuin on B16F10 melanoma cells is 15 μM.

B16F10 melanoma cells were plated in a 96-well tissue culture plate with 2,000 cells in 50 µl of medium (DMEM+10% fetal bovine serum+1% penicillin-streptomycin) per well. After 24 hours, the targeted curcumin derivative (linked to 633 dye) was administered in a range of concentrations-10 nM, 20 nM, 30 nM, 50 nM, 100 nM. The product was diluted in neurobasal medium (+1% penicillin-streptomycin, 1% 1-glutamine, 2% B27 supplement), with 50 µl per well, and 2 wells per concentration. Control wells were treated with corresponding concentrations of free MUC18 antibody coupled to 633 dye. The plate was imaged after 24 hours using visible light and fluorescent microscopes. Using cell counts from four frames per well, the mean live cell number and mean standard deviation for each concentration (and its corresponding control) were found. The data was compiled and graphed on Kaleida Graph. The resulting IC50 value obtained from three discrete experiments was 25 nM for antibody-linked curcumin, whereas the IC50 for free curcumin was 15 µM. See below. Each corresponding control well received the same amount of curcumin-free MelCAM-Dylight800. See FIG. 1.

Figure 2:
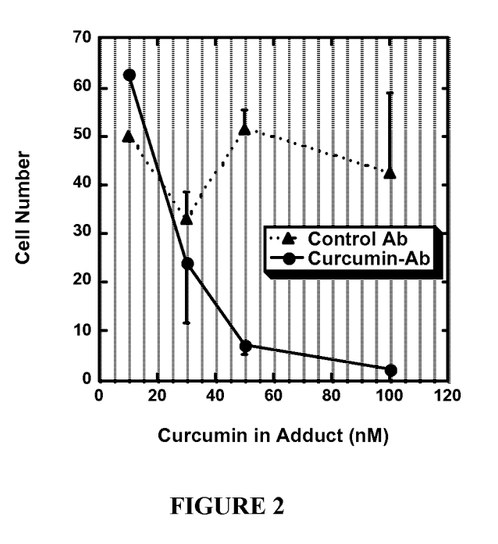
FIG. 2: The IC50 for the effect of MUC18 antibody-curcumin adduct on B16F10 melanoma cells is 25 nM.

3B) Free Curcumin IC50:

Determined using same methods as step 1a. Dilution of 100 nM, 200 nM, 300 nM, 400 nM, 500 nM, 1 µM, 10 µM, 20 µM, 30 µM, 40 µM, and 50 µM were made using a 40 mM stock solution of curcumin in DMSO. Curcumin IC50 was compared to curc-MUC18 IC50 using Kaleida Graph. As can be seen in FIG. 2, solubilized, non-antibody linked curcumin eliminates B16F10 melanoma cells in vitro with an IC50 of about 15 µM.

3C) Adduct Treatment of Brain Tumor-Containing Mice:

Brain tumors were generated through transcranial implantation of 1000 B16F10 cells into the right front brain (Purkayastha, S., Berliner, A., Fernando, S. S., Ranasinghe, B., Ray, I., Tariq, H., and Banerjee, P., *Brain Research* 1266C, 130-138) (2009)). Curcumin plus Dylight800-labeled Ab (Curcumin) or Dylight800-labeled Ab (control) (5 µl of each) was stereotaxically injected into the tumor at day 8 after implantation of B16F10 cells (in C57BL mice) followed by in vivo imaging. The control mice received the same amount of curcumin-free MelCAM (MUC18) antibody-Dylight800 adduct as the test mice received curcumin-linked MelCAM (MUC18) antibody-Dylight800 adduct. One set of dye-Ab-injected mice and one set of curcumin-Ab-dye-injected mice were sacrificed after 24 h (day 9) and their brains scanned for fluorescence using the Odyssey near-IR scanner. A second set of dye-Ab-injected and curcumin-Ab-dye-injected mice were sacrificed on day 13. On day 9, the carrier-injected mouse had a sizeable brain tumor, in which the green fluorescent, dye-Ab complex was heavily concentrated. Bright field images show some dark melanoma cells on the front surface of the brain. At day 13, the tumor covered almost the entire brain, as shown by both fluorescence imaging as well as bright field images. In contrast, at both day 9 and day 13, the curcumin-Ab-dye-injected mice contained a significantly reduced number of tumor cells, which could be detected only by fluorescence imaging.

3D) Repeat Experiment:

Brain tumors were generated in two sets of mice as in Experiment 3C. On day 8, one set of mice received the curcumin-Ab-Dylight800 adduct and the other (control) received the Ab-Dylight800 adduct, also as in Experiment 3C. On days 11, 13, and 15, the curcumin each adduct-treated mouse also received 5 µl of 3 mM curcumin in DMSO:PBS as reported earlier (Purkayastha, S., Berliner, A., Fernando, S. S., Ranasinghe, B., Ray, I., Tariq, H., and Banerjee, P., *Brain Research* 1266C, 130-138) (2009)), whereas the control mice received 5 µl of the carrier.

Tumor-containing mice were recovered after transcranial injection of curcumin-Ab-Dylight800 adduct on day 8, followed by solubilized curcumin on days 11, 13, and 15, and were still alive on day 20. Mice receiving control antibody, and then carrier die of brain tumor on day 15.

Example 4

CD68 Antibody-Curcumin Conjugates Show a Higher Potency to Kill Glioblastoma GL261 Cells than Solubilized Curcumin The same approach used for the B16F10 melanoma cells (see above) was next used for the glioblastoma GL261 cells by attaching curcumin to an antibody against the CD68 antigen, which is expressed on the surface of grade III/IV glioblastoma (Strik, H. M., et al., *Galectin*-3: *Cellular Distribution and Correlation with WHO-grade in Human Gliomas*. Journal of Neuro-Oncology, 53(1): p. 13-20 (2001)). Targeted curcumin was again more effective in eliminating the GL261 mouse glioma cells (the decrease in IC50 was from 10 µM for solubilized curcumin to 70 nM for antibody targeted curcumin: a 143-fold decrease). See FIGS. 3 and 4, respectively. Newcomb and Zagzag have described the GL261-implanted C57BL6 mice as a model for glioblastoma brain tumor. See Newcomb, E. W., and Zagzag, D., *The Murine GL261 Glioma Experimental Model to Assess Novel Brain Tumor Treatments*, in *CNS Cancer*, 2009, p. 227-241.

Figure 3:
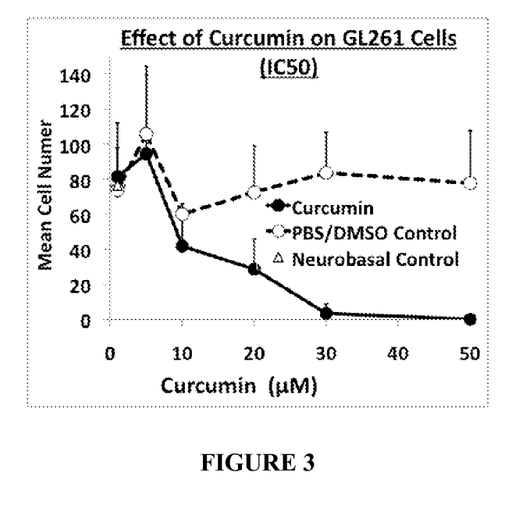
FIG. 3: The IC50 for the effect of solubilized curcuin on GL261 glioblastoma cells is 10 μM.
Figure 4:
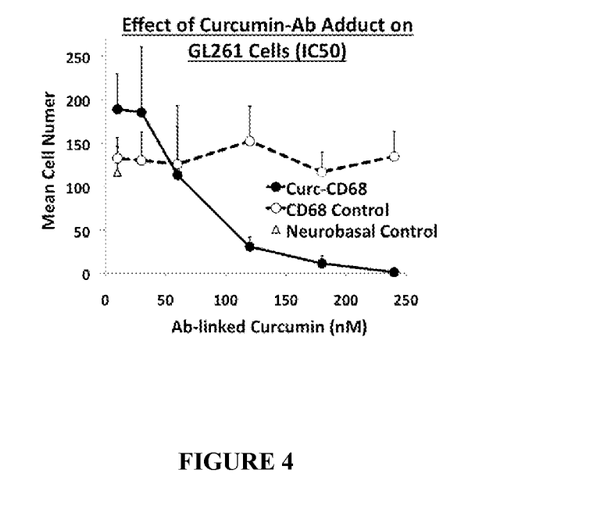
FIG. 4: The IC50 for the effect of CD68 antibody-curcuin adduct on GL261 glioblastoma cells is 70 nM.
Figure 5:
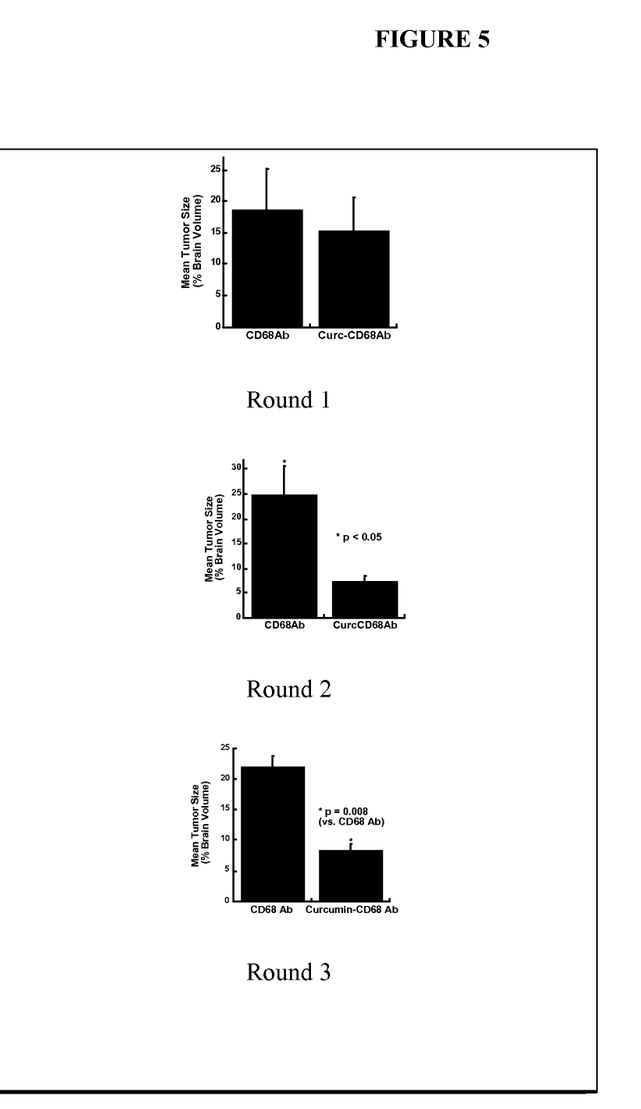

The IC50 for non-targeted curcumin was 10 µM, whereas the IC50 for CD68 antibody-attached curcumin was 70 nM. Accordingly, non-targeted curcumin kills GL261 cells in the micromolar range. Ab-linked curcumin kills GL261 cells in the nanomolar range.

Example 5

Curcumin-CD68 Antibody Conjugate Causes Shrinkage of GL261 Brain Tumors

Dylight800-CD68 antibody labeling near death showed a significant reduction in tumor size in the 750 pmole antibody-linked curcumin, but not in 37.5 pmole Ab-linked curcumin-treated mice. 750 pmole of this preparation of antibody-linked curcumin increased longevity, but it did not completely rescue the mice. It should be noted that due to a procedural shortcoming, the adduct prepared for these experiments also showed significantly lower anti-G1261 activity in vitro. We expect that an optimal preparation of the adduct will rescue mice from glioblastoma tumors.

We claim:

1. A curcumin derivative having the formula I:

$$Z\text{-}L\text{-}Y \qquad (I)$$

wherein:

Z represents:

A represents —CH$_2$—CH$_2$— or —CH=CH—;
L represents —C(O)—(NH)$_{n1}$—R—(NH)$_{n2}$—C(O)—;

R represents a saturated or unsaturated, branched or unbranched hydrocarbyl chain having a minimum of 3 carbon atoms in the chain; wherein the maximum number of carbon atoms in the chain is 24; and wherein the carbon atoms of the chain can be replaced by at least one heteroatom, wherein the heteroatoms are independently —O— or —NH$_2$—, with the proviso that each heteroatom is separated from each other heteroatom by at least two carbon atoms;

n1 and n2 independently represent 0 or 1; and

Y represents a CD68 antibody.

2. A curcumin derivative according to claim 1, wherein A represents —CH═CH—.

3. A curcumin derivative according to claim 1, wherein n1 and n2 are 0.

4. A curcumin derivative according to claim 1, wherein R represents a saturated, unbranched hydrocarbyl chain.

5. A curcumin derivative according to claim 1, wherein R represents a saturated, unbranched hydrocarbyl chain having a minimum of 3 and a maximum of 8 carbon atoms.

6. A curcumin derivative according to claim 1, wherein a lysine residue of antibody Y bonds to L.

7. A method of inhibiting the growth of a brain tumor in a human in need thereof, the method comprising administering to the human an effective amount of a curcumin derivative having the formula I:

Z-L-Y  (I)

wherein:

Z represents:

A represents —CH$_2$—CH$_2$— or —CH═CH—;

L represents —C(O)—(NH)$_{n1}$—R—(NH)$_{n2}$—C(O)—;

R represents a saturated or unsaturated, branched or unbranched hydrocarbyl chain having a minimum of 3 carbon atoms in the chain; wherein the maximum number of carbon atoms in the chain is 24; and wherein the carbon atoms of the chain can be replaced by at least one heteroatom, wherein the heteroatoms are independently —O— or —NH$_2$—, with the proviso that each heteroatom is separated from each other heteroatom by at least two carbon atoms;

n1 and n2 independently represent 0 or 1; and

Y represents an antibody that binds specifically to the CD68 antigen of a brain tumor cell.

8. The method according to claim 7, wherein A represents —CH═CH—.

9. The method according to claim 7, wherein n1 and n2 are 0.

10. The method according to claim 7, wherein R represents a saturated, unbranched hydrocarbyl chain.

11. The method according to claim 7, wherein R represents a saturated, unbranched hydrocarbyl chain having a minimum of 3 and a maximum of 8 carbon atoms.

12. The method according to claim 7, wherein a lysine residue of antibody Y bonds to L.

13. The method according to claim 7, wherein the tumor is a glioblastoma.

14. The method according to claim 7, further comprising, after substantially all tumor cells have been eliminated, administering an amount of a solubilized form of curcumin effective to slow the growth of any remaining tumor cells.

15. The method according to claim 7, further comprising administering at least one additional anti-cancer chemotherapeutic agent selected from the group consisting of carboplatin, cisplatin, cyclophosphamide, docetaxel, doxorubicin, erbitux, erlotinib, etoposide, fluorouracil, gemcitabine, herceptin, imatinib, irinotecan mesylate, irinotecan, methotrexate, paclitaxel, sorafinib, sunitinib, topotecan, vinblastine, and vincristine.

16. The method according to claim 7, further comprising administering at least one additional anti-cancer chemotherapeutic agent selected from the group consisting of Temodar, Avastin, Matulane, Gliadel, and BiCNU.

17. The method according to claim 7, wherein the brain tumor originated in the brain or is a metastasis to the brain that originated elsewhere.

* * * * *

UNITED STATES PATENT AND TRADEMARK OFFICE
CERTIFICATE OF CORRECTION

PATENT NO. : 9,446,145 B2  Page 1 of 1
APPLICATION NO. : 13/513348
DATED : September 20, 2016
INVENTOR(S) : Banarjee et al.

It is certified that error appears in the above-identified patent and that said Letters Patent is hereby corrected as shown below:

On the Title Page

Item [75] delete "RAJA Krishnaswami" and insert -- Krishnaswami RAJA --

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*